United States Patent [19]

Helms et al.

[11] Patent Number: 4,499,418
[45] Date of Patent: Feb. 12, 1985

[54] WATER CUT MONITORING MEANS AND METHOD

[75] Inventors: David A. Helms; Gregory J. Hatton; Thomas M. Williams, all of Houston, Tex.

[73] Assignee: Texaco Inc., White Plains, N.Y.

[21] Appl. No.: 405,458

[22] Filed: Aug. 5, 1982

[51] Int. Cl.³ .................................... G01N 22/04
[52] U.S. Cl. .................... 324/58.5 A; 324/58.5 B; 73/61.1 R
[58] Field of Search .............. 73/61.1 R; 324/58.5 A, 324/58.5 B, 58.5 R; 340/603

[56] References Cited

U.S. PATENT DOCUMENTS

| 2,749,443 | 6/1956 | Dicke et al. | 324/58.5 R X |
|---|---|---|---|
| 3,498,112 | 3/1970 | Howard | 73/61.1 R |
| 3,693,079 | 9/1972 | Walker | 324/58.5 A |
| 4,206,399 | 6/1980 | Fitsky et al. | 324/58.5 B X |
| 4,311,957 | 1/1982 | Hewitt et al. | 324/58.5 R |
| 4,361,801 | 11/1982 | Meyer et al. | 324/58.5 R |
| 4,368,641 | 1/1983 | McLeod, Jr. | 324/58.5 B X |

FOREIGN PATENT DOCUMENTS

| 254591 | 4/1970 | U.S.S.R. | 324/58.5 A |
|---|---|---|---|
| 288407 | 1/1971 | U.S.S.R. | 324/58.5 B |
| 864094 | 9/1981 | U.S.S.R. | 73/61.1 R |

OTHER PUBLICATIONS

"Paper Sheet Moisture Measurements by Microwave Phase Perturbation Techniques", Journal of Microwave Power; pp. 25–34; 5(1), 1970, Bosisio et al.

"Phase-Sensitive Ultra High-Frequency Moisture Gauge", Ind. Lab. (U.S.A.), vol. 37, No. 10, 10–1971; pp. 1624–1626; Berliner et al.

"An Improved Microwave Method of Moisture Content Measurement & Control; IECI-23, No. 4, pp. 364–370; 11-1976; Kraszewski et al.

"Microwave Attenuation Measurement with Chopped Subcarrier Method for On-Line Moisture Monitoring", Microwave Power Symposium 1978 Ottawa, Canada; 6-1978; pp. 142–144.

Primary Examiner—Gerald Goldberg
Assistant Examiner—Tom Noland
Attorney, Agent, or Firm—Robert A. Kulason; Ronald G. Gillespie

[57] ABSTRACT

A water cut monitor includes a microwave transmitter which transmits microwave energy through a fluid mixture containing water. An indicator connected to the microwave transmitter and receiving the microwave energy transmitted through the emulsion provides an indication of the water fraction of the fluid mixture in accordance with the phase difference between the microwave energy from the transmitter means and the microwave energy transmitted through the fluid mixture.

4 Claims, 1 Drawing Figure

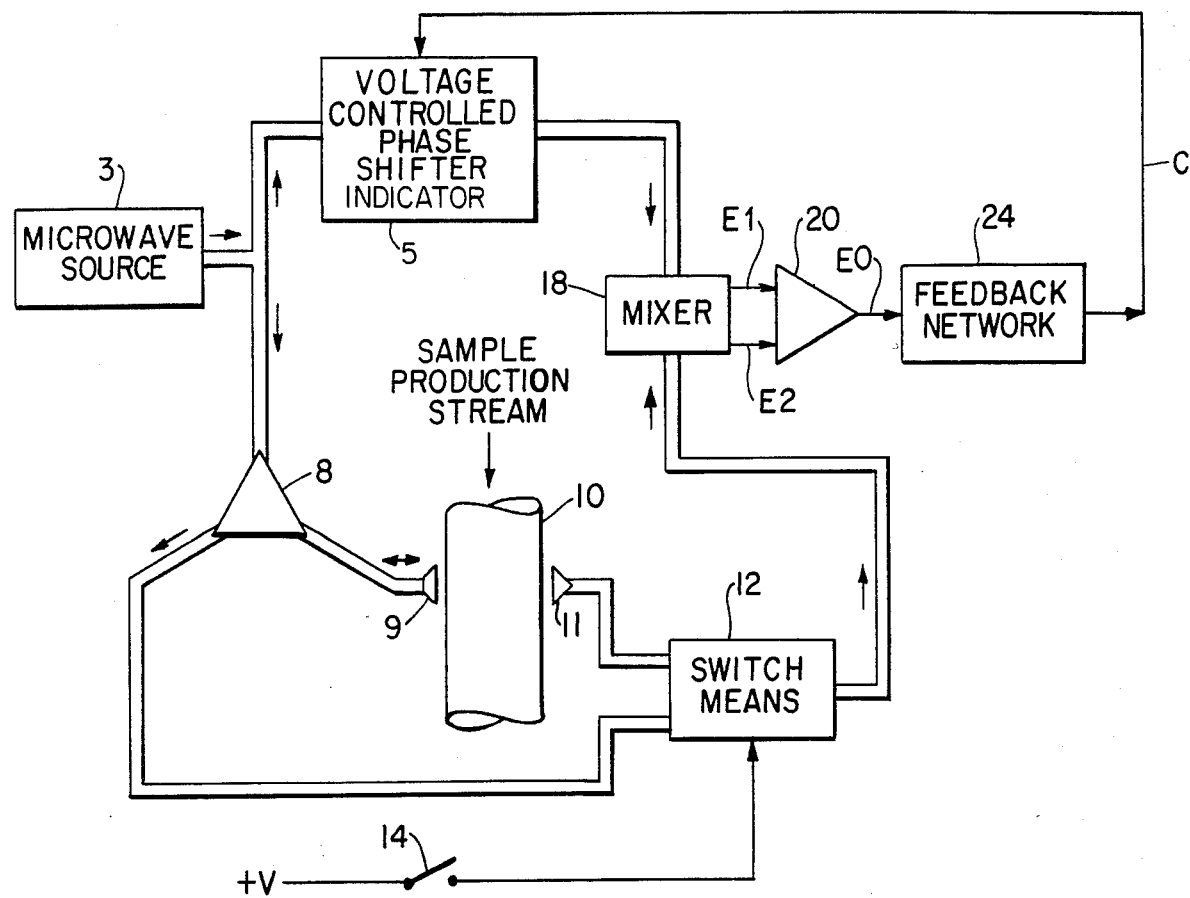

4,499,418

WATER CUT MONITORING MEANS AND METHOD

BACKGROUND OF THE INVENTION

Field of the Invention

The present invention relates to monitoring means and methods in general and, more particularly, to water cut monitoring means and methods.

SUMMARY OF THE INVENTION

A water cut monitor includes a microwave transmitter which transmits microwave energy through a fluid mixture containing water. An indicator connected to the microwave transmitter and receiving the microwave energy transmitted through the fluid mixture provides an indication of the water fraction of the fluid mixture in accordance with the phase difference between the microwave energy from the transmitter means and the microwave energy transmitted through the fluid mixture.

The objects and advantages of the invention will appear more fully hereinafter, from the consideration of the detailed description which follows, taken together with the accompanying drawings, wherein one embodiment is illustrated by way of example. It is to be expressly understood, however, that the drawings are for illustrative purposes only, and are not to be construed as defining the limits of the invention.

DESCRIPTION OF THE DRAWING

The FIGURE shows a water cut monitor, constructed in accordance with the present invention, in simplified block diagram form.

DESCRIPTION OF THE INVENTION

The water cut monitor shown in the FIGURE includes a microwave transmitter 3 providing electromagnetic energy, hereinafter referred to as microwave energy, at a microwave frequency. Transmitter 3 is low powered and may use a microwave Gunn source. Further details of transmitter 3 are not necessary to an understanding of the present invention. Transmitter 3 provides the microwave energy to a conventional type voltage controlled phase shifter 5 and to a circulator 8.

Circulator 8 provides the microwave energy from transmitter 3 to an antenna 9 for transmission through a sample stream of a fluid mixture passing through a test cell 10. The transmitted microwave energy passes through the fluid mixture and is received by an antenna 11 which provides the received microwave energy to switch means 12. The fluid mixture also reflects some microwave energy back to antenna 9 which passes back through antenna 9 to circulator 8. Circulator 8 blocks the reflected microwave energy from feeding back to transmitter 3 and provides the reflected microwave energy to switch means 12. Reflected microwave energy becomes more important as the distance between antennas 9 and 11 increases. This is especially true where a large pipeline carrying a fluid mixture is being monitored.

A positive direct current voltage +V is provided to a switch 14 which is connected to switch means 12. With switch 14 open, switch means 12 provides the microwave energy from antenna 11 as a test microwave energy. When switch 14 is closed, the reflected microwave energy from circulator 8 is provided by switch means 12 as the test microwave energy.

The microwave energy from voltage control phase shifter 5, hereinafter called the reference microwave energy, and the test microwave energy from switch means 12 are provided to a mixer 18 which mixes them to provide two electrical signals E1, E2 representative of the phases of the reference microwave energy and the test microwave energy.

A differential amplifier 20 provides an output signal Eo in accordance with the difference between signals E1 and E2. Signal Eo is a function of the phase difference between the reference microwave energy and the test microwave energy. Signal Eo may be applied to an indicator in which the amplitude of Eo will be representative of the phase difference or as shown in the present example it may be provided to a feedback network 24. Feedback network 24 provides a control voltage to voltage control phase shifter 5 controlling the phase of the reference microwave energy. Signal Eo, and hence the control voltage C, decreases in amplitude until there is substantially 90° phase difference between the reference microwave energy and the test microwave energy. Voltage control phase shifter 5 indicates the amount of phase shift required to eliminate the phase difference. This is accomplished by providing signal Eo to an integrating feedback network 24 which provides control voltage C back to phase shifter 5. The amplitude of voltage C corresponds to the necessary phase shift.

The present invention as hereinbefore described is a microwave water cut monitor that determines the water cut of a fluid mixture by monitoring the phase difference between a reference microwave energy and microwave energy that has passed through the fluid mixture or has been reflected by the fluid mixture.

What is claimed is:

1. A water cut monitor comprising
   test cell means for having a fluid mixture flowing through it,
   means for transmitting microwave energy into a flowing fluid mixture in the test cell means, said means for transmitting microwave energy comprising microwave source means and transmitting antenna means, and
   indicator means for providing an indication of the water cut of the fluid mixture in accordance with the phase difference between the transmitted microwave energy and either microwave energy that has passed through the flowing fluid mixture or microwave energy that is reflected from the flowing fluid mixture said indicator means includes
      circulator means connected between said microwave source means and said transmitting antenna means for providing the microwave energy from said source means to said transmitting antenna means and for providing the reflected microwave energy in accordance with the microwave energy which has been reflected by the flowing fluid mixture,
   receiving means for receiving the microwave energy that has passed through the flowing fluid mixture to provide received microwave energy,
   means for providing a control signal, and
   switch means connected to the control signal means, to the receiving means and to the circulator means for selecting either the received microwave energy from the receiving means or the reflected microwave energy from the circulator means in accordance with the control signal so that the reference microwave energy is utilized with either the microwave energy that has passed through the fluid mixture or the reflected microwave energy.

2. A monitor as described in claim 1 in which the transmitting means includes a microwave source providing microwave energy to the indicating means, and a transmitting antenna connected to the microwave source which transmits the microwave energy into the flowing fluid; and the receiving means includes a receiving antenna spatially arranged with the transmitting antenna so that the flowing fluid mixture in the test cell flows between said antennas, and said receiving antenna provides the microwave energy that has passed through the fluid mixture as the received microwave energy.

3. A monitor as described in claim 2 in which the indicator means further comprises:

a voltage controlled phase shifter receiving the transmitted microwave energy from said transmitting means for phase shifting the transmitted microwave energy in accordance with a phase shift signal to provide a reference microwave energy, and phase shift signal means receiving the reference microwave energy and the received microwave energy for providing the phase shift signal to the phase shifter until there is substantially a 90° phase difference between the reference microwave energy and the received microwave energy at which time the phase shifter indicated phase shift corresponds to the water fraction of the fluid mixture.

4. A monitor as described in claim 3 in which the phase shift signal means includes:

mixer means connected to the phase shifter and to the switch means for mixing the reference microwave energy from the phase shifter with the microwave energy from the switch means to provide two signals representative of the phases of the reference microwave energy and the microwave energy from the switch means, a differential amplifier connected to the mixer means for providing an output signal in accordance with the difference between the two signals from the mixer means, and a feedback network connected to the phase shifter and to the differential amplifier which provides the phase shift signal in accordance with the output signal.

* * * * *